(12) United States Patent
de Graaf et al.

(10) Patent No.: US 9,846,209 B2
(45) Date of Patent: Dec. 19, 2017

(54) HOMOGENIZATION DEVICE FOR HOMOGENIZATION OF A MAGNETIC FIELD

(71) Applicant: Krohne AG, Basel (CH)

(72) Inventors: Ariël de Graaf, Utrecht (NL); Henry van der Linden, Utrecht (NL); Jan Teunis Aart Pors, Oud-Beijerland (NL); Jan-Willem Ramondt, Breda (NL)

(73) Assignee: Krohne AG, Basel (CH)

( * ) Notice: Subject to any disclaimer, the term of this patent is extended or adjusted under 35 U.S.C. 154(b) by 529 days.

(21) Appl. No.: 14/462,746

(22) Filed: Aug. 19, 2014

(65) Prior Publication Data

US 2015/0070018 A1   Mar. 12, 2015

(30) Foreign Application Priority Data

Aug. 20, 2013  (DE) .................. 10 2013 013 719

(51) Int. Cl.
*G01R 33/38*  (2006.01)
*G01R 33/3873*  (2006.01)
(Continued)

(52) U.S. Cl.
CPC ......... *G01R 33/3873* (2013.01); *G01F 1/716* (2013.01); *G01F 15/00* (2013.01);
(Continued)

(58) Field of Classification Search
CPC ... G01F 1/716; G01F 1/56; G01F 1/74; G01F 5/00; G01R 33/56308; G01R 33/44;
(Continued)

(56) References Cited

U.S. PATENT DOCUMENTS 3,564,400 A    2/1971  Pike et al.
4,771,244 A *  9/1988  Vermilyea .......... G01R 33/3873
                                                    324/320

(Continued)

FOREIGN PATENT DOCUMENTS

CN    102870174 A  *  1/2013  ......... G01R 33/3815
GB    2405935 A       3/2005
JP    H01280447 A    11/1989
WO    2011122403 A1  10/2011

OTHER PUBLICATIONS

Translation of CN 102870174 A.*

(Continued)

*Primary Examiner* — Clayton E Laballe
*Assistant Examiner* — Ruifeng Pu
(74) *Attorney, Agent, or Firm* — David S. Safran

(57) ABSTRACT

A homogenization device for homogenization of a magnetic field with an non-magnetic carrier and compensation elements formed of a magnetic material, the carrier having a carrier wall and the carrier wall surrounding a carrier interior, in the homogenization device located in the magnetic field the magnetic field penetrating into the carrier interior through a first carrier region of the carrier wall and emerging from the carrier interior through a second carrier region of the carrier wall and each of the compensation elements which are located on the carrier contributing to the homogenization of the magnetic field at least in the carrier interior. In the homogenization device, handling during homogenization is improved in that there are recesses in the carrier wall and in each of the recesses at least one of the compensation elements can be directly inserted and removed.

14 Claims, 1 Drawing Sheet

(51) Int. Cl.
*G01F 1/716* (2006.01)
*G01R 33/24* (2006.01)
*G01R 33/34* (2006.01)
*G01R 33/3875* (2006.01)
*G01F 15/00* (2006.01)
*G01N 24/08* (2006.01)

(52) U.S. Cl.
CPC ....... *G01R 33/24* (2013.01); *G01R 33/34046* (2013.01); *G01R 33/3875* (2013.01); *G01N 24/08* (2013.01)

(58) Field of Classification Search
CPC .. G01R 33/20; G01R 33/4831; G01R 33/343; G01R 33/448; G01R 33/56316; G01R 33/60; G01R 33/34007; G01R 33/34061; G01R 33/34; G01R 33/365; G01R 33/3657; G01R 33/383; G01R 33/3873; G01R 33/465; G01R 33/445; G01N 24/082; G01N 24/08; A61B 5/0263; A61B 5/0265
See application file for complete search history.

(56) References Cited

U.S. PATENT DOCUMENTS

| | | | |
|---|---|---|---|
| 4,901,018 A | | 2/1990 | Lew |
| 5,426,676 A | * | 6/1995 | Hopkins ................ F16J 15/127 376/203 |
| 5,431,165 A | * | 7/1995 | Sellers ................ G01R 33/3873 324/318 |
| 5,923,235 A | | 7/1999 | Van Oort |
| 5,999,076 A | | 12/1999 | Becker, Jr. et al. |
| 6,351,125 B1 | * | 2/2002 | Westphal ........... G01R 33/3873 324/319 |
| 7,245,128 B2 | | 7/2007 | Ando et al. |
| 2014/0306702 A1 | * | 10/2014 | Lazar .................... G01R 33/34 324/307 |

OTHER PUBLICATIONS

Windt et al., "A Portable Halbach Magnet That Can be Opened and Closed Without Force: The NMR-CUFF", Journal of Magnetic Resonance, vol. 208, 2011, pp. 27-33.

* cited by examiner

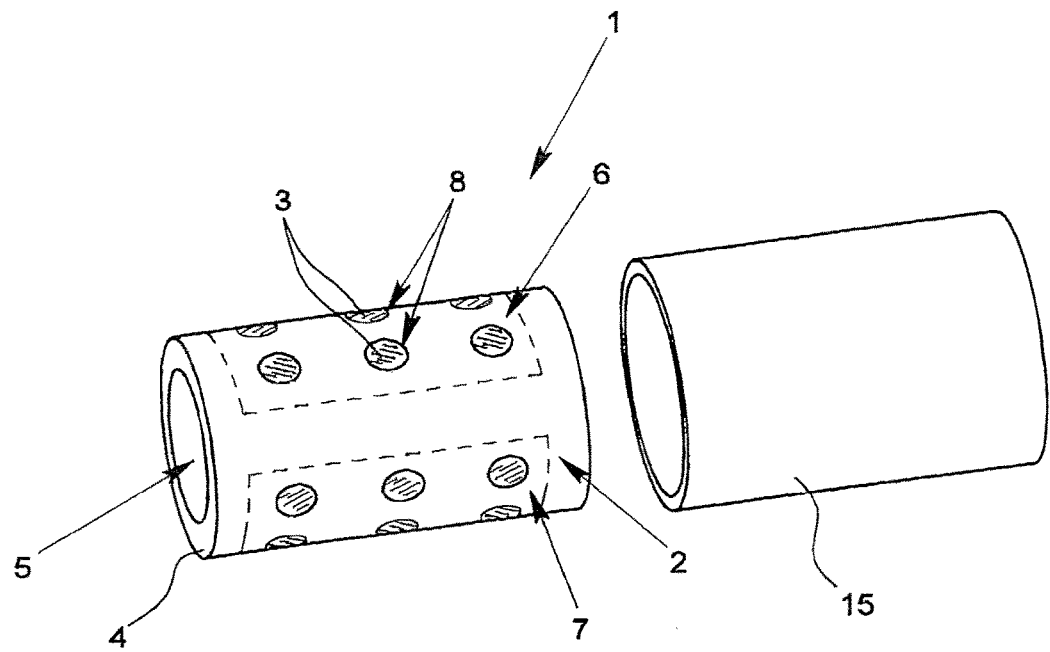
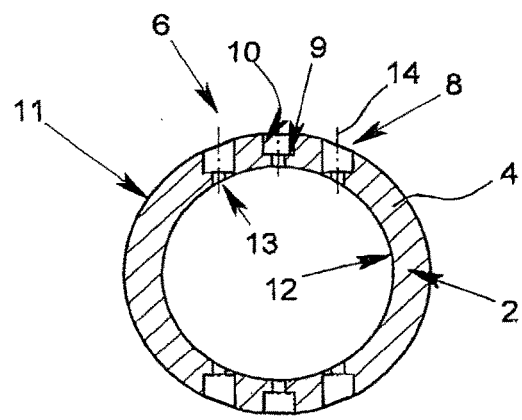
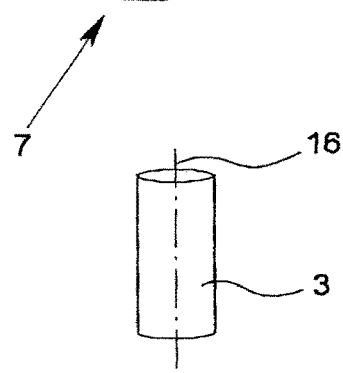
Fig. 1
Fig. 2
Fig. 3

HOMOGENIZATION DEVICE FOR HOMOGENIZATION OF A MAGNETIC FIELD

BACKGROUND OF THE INVENTION

Field of the Invention

The invention relates to a homogenization device for homogenization of a magnetic field with a non-magnetic carrier and compensation elements which formed at least partially of a magnetic material, the carrier having a carrier wall and the carrier wall surrounding a carrier interior. In the homogenization device located in the magnetic field, the magnetic field penetrates into the carrier interior through a first carrier region of the carrier wall and emerges from the carrier interior through a second carrier region of the carrier wall and each of the compensation elements which are located on the carrier contribute to the homogenization of the magnetic field at least in the carrier interior.

Description of Related Art

Homogenization devices of the initially mentioned type can be used in various applications for homogenization of a magnetic field. Only one exemplary application of the homogenization devices is the homogenization of the magnetic field of a nuclear magnetic flowmeter. Nuclear magnetic flowmeters determine the flow rate of a medium which is flowing through a measuring tube from the nuclear magnetic resonance measurements which have been taken on the medium.

Nuclear magnetic resonance measurements require media with elements whose atomic nuclei have a magnetic moment. This is given in atomic nuclei with a nuclear spin. The nuclear spin can be understood as an angular momentum which can be described by a vector, and accordingly, the magnetic moment can also be described by a vector which is aligned parallel to the vector of the angular momentum. In the presence of a magnetic field, the vector of the magnetic moment of an atomic nucleus is aligned parallel to the vector of the magnetic field at the location of the atomic nucleus. Here, the vector of the magnetic moment of the atomic nucleus precesses by the vector of the macroscopic magnetic field at the location of the atomic nucleus. The frequency of the precession is called the Larmor angular frequency $\omega_L$ and is proportional to the amount of the magnetic flux density B. The Larmor frequency is computed according to the formula $\omega_L = \gamma B$, in which $\gamma$ is the gyromagnetic ratio which is maximum for hydrogen nuclei and $\gamma = 276.5 \cdot 10^6$ rad/(sT).

Nuclear magnetic resonance measurement methods excite the atomic nuclei of a medium which have a magnetic moment in the presence of a magnetic field and measure the action of the excitation. In nuclear magnetic flowmeters, the flow rate of the medium through the measuring tube is determined using the measured action of the excitation. An excitation of the atomic nuclei causes an in-phase precession of the atomic nuclei with the Larmor angular frequency $\omega_L$ of the atomic nuclei which are precessing beforehand with statistically distributed phases to one another and the excitation perturbs the previously prevailing equilibrium state of the precessing atomic nuclei. The perturbation, as long as the precession is in-phase, is measurable as a macroscopic alternating magnetic field, the angular frequency of the alternating magnetic field being the Larmor angular frequency.

To perform the nuclear magnetic resonance measurements, nuclear magnetic flowmeters have a magnetic field generating apparatus for generating the magnetic field in the medium which is flowing through the measuring tube. Here, the conventional magnetic flux density in the flowing medium is $B \approx 0.3$ T. A fluctuation of the magnetic flux density in the medium on the order of magnitude of the magnetic flux density of the terrestrial magnetic field, for example, by $\Delta B = 30$ μT, leads to a fluctuation of the Larmor frequency by $\Delta \omega_L = 276.5 \cdot 10^6$ rad(sT)·30 μT$\approx 8.1 \cdot 10^3$ 1/s of the precessing atomic nuclei which are flowing in the medium. The fluctuation of the Larmor frequency itself leads to a deterioration of measurement accuracy and also causes a loss of the in-phase precession of the atomic nuclei, as a result of which the amplitude of the macroscopic alternating magnetic field decreases; this leads to a further deterioration of measurement accuracy.

Conventional magnetic field generating apparatus of nuclear magnetic flowmeters are built out of permanent magnets, the permanent magnets generally being arranged as Halbach arrays. But, generally the required measurement accuracy of nuclear magnetic flowmeters does not result from the homogeneity of a magnetic field which has been produced in this way, for which reason it is necessary to homogenize the magnetic field by a homogenization device. However, magnetic fields which have been produced with electromagnets often do not meet the demands on the homogeneity of the magnetic field which are imposed by the application.

A homogenization device of the initially described type in particular for homogenization of the magnetic field which has been generated by the magnetic field generation apparatus of a nuclear magnetic flowmeter can be located in the medium flowing through the measuring tube in the magnetic field such that the measuring tube lies in the interior of the carrier of the homogenization device in accordance with the invention and is surrounded by the carrier wall of the measuring tube. The magnetic field of the magnetic field generation apparatus penetrates into the carrier interior through the first carrier region of the carrier wall and emerges from the carrier interior through the second carrier region of the carrier wall. The compensation elements located on the carrier homogenize the magnetic field in doing so at least in the carrier interior and thus also in the medium.

The carrier of a homogenization device is formed of non-magnetic materials. Non-magnetic materials are wherein they influence a magnetic field, if at all, only to a degree which is negligibly small for the respective application. Diamagnetic and paramagnetic materials are also regarded as non-magnetic materials. In contrast, the compensation elements consist at least partially of a magnetic material. Magnetic materials are ferromagnetic, ferrimagnetic and antiferromagnetic materials. It is common to them that they influence a magnetic field.

In the prior art, a homogenization device of the initially described type is known in which each of the compensation elements is arranged on the carrier by cementing. The disadvantages of this homogenization device are apparent in the examination of the process of homogenization of a magnetic field which encompasses several steps.

In a first step, the magnetic field is measured and usually several of the compensation elements are arranged on the carrier at certain positions according to the measurement results. In a second step, the magnetic field with homogenization devices which are located in the magnetic field is measured in the carrier interior. In this second step, the magnetic field in the carrier interior is usually more homogenous than without the homogenization device, but the homogeneity of the magnetic field often still does not meet the demands of the application. Consequently, a third step is necessary in which compensation elements arranged according to the measurement results from the previous step are removed or shifted. In a fourth step, the magnetic field with the homogenization device located in the magnetic field is again measured in the carrier interior. In this fourth step, the magnetic field in the carrier interior is usually more homogeneous than after the first step. If the homogeneity of the magnetic field meets the demands, the process of homogenization is completed, otherwise the third and fourth step are repeated until the homogeneity meets the demands of the application. Accordingly, the homogenization of the magnetic field is an iterative process.

In the homogenization device known in the prior art, to remove and shift each individual one of the compensation elements, the cementing must be dissolved and the residues of the cement must be removed. If a cement is used whose cementing performance is low for simple removal of the compensation elements, the operating reliability of the cementing is adversely affected and additional measures must be taken to fix the compensation elements which have been cemented tight. If an adhesive is used whose adhesive performance is high for ensuring the operating reliability of the cementing, damage to the carrier is possible when the compensation elements are removed. Moreover, the reproducibility of the arrangement of the compensation elements at predetermined positions is subject to disruptively large inaccuracies.

SUMMARY OF THE INVENTION

Therefore, the primary object of this invention is to devise a homogenization device for homogenization of a magnetic field in which the handling of the homogenization device during homogenization is improved.

The homogenization device in accordance with the invention in which the above described object is achieved is, first of all, essentially wherein there are recesses in the carrier wall and in each of the recesses at least one of the compensation elements can be directly inserted and removed.

The homogenization device in accordance with the invention, as compared to the homogenization devices known from the prior art, first of all, has the advantage that the compensation elements can be arranged on the carrier without cementing. This improves the placement, removal and also the shifting of compensation elements. Moreover, inserting the compensation elements into the recesses also yields improved reproducibility of the arrangement of the compensation elements at predetermined positions.

Usually, for homogeneity of the magnetic field in the carrier interior which is sufficient for an application, the compensation elements are inserted only in a subset of the recesses. Mostly, only one of the compensation elements at a time is also inserted in the recesses. But, to achieve sufficient homogeneity of the magnetic field, also at least two of the compensation elements together can be inserted in the recesses. Preferably, the compensation elements which together can be inserted into one of the recesses have the same geometry as an individual one of the compensation elements which can be inserted into this recess, (Generally, the geometry of a body is determined by its shape and its size). Moreover, it is also provided that the position and alignment of one of the compensation elements which has been inserted in one of the recesses with reference to the ideal magnetic field vector in the recess can be set by filler elements between the compensation element and the recess. The ideal magnetic field vector is that of a homogeneous magnetic field in the carrier interior.

The compensation elements which have been inserted into the recesses are fixed by adhesive friction between the recesses and the inserted compensation elements (friction fit), at least to the degree that the adhesive force dictated by the adhesive friction is at least as large as the force due to the weight of the respective inserted compensation elements and that the adhesive force is at least the same size as the forces which are exerted by the compensation elements on one another. The adhesive force can be set by matching the geometry of the recesses to the geometry of the compensation elements which have been inserted into the recesses.

The shape of the recesses can be diverse. For the sake of simple production by drilling, in particular, circular cylindrical recesses have proven themselves. However, polygonal recesses, for example, cuboidal recesses, are advantageous, production taking place preferably by milling. The shape of the compensation elements can also be diverse. Here, circular cylindrical and polygonal compensation elements have proven themselves and from the polygonal, especially cuboidal compensation elements are particularly useful. Not only circular cylindrical compensation elements, but also polygonal compensation elements can be inserted into circular cylindrical recesses and conversely circular cylindrical compensation elements can also be inserted into polygonal recesses. But, the insertion of polygonal compensation elements into correspondingly polygonal recesses is especially advantageous because rotation of the inserted compensation elements is not possible.

In one preferred configuration of the homogenization device in accordance with the invention, there is at least one of the recesses in the first carrier region and/or there is at least one of the recesses in the second carrier region. In a first alternative configuration, it is provided that only in the first carrier region is there at least one of the recesses and in a second alternative configuration it is provided that only in the second carrier region is there at least one of the recesses. Recesses both in the first carrier region and also in the second carrier region ensure the greatest possible freedom in the arrangement of compensation elements, while in the two alternative configurations, the production effort is reduced by the smaller number of recesses, but nevertheless homogenization of the magnetic field which is sufficient for many applications is attainable.

In another preferred configuration of the homogenization device in accordance with the invention, it is provided that at least one subset of the recesses forms a regular pattern in the carrier wall. A regular pattern enables the magnetic field in the carrier interior to be uniformly influenced. A checkerboard pattern is a good regular pattern. A checkerboard pattern is wherein the recesses are joined by straight lines which intersect at right angles and that the distances of adjacent recesses are the same. The pattern is accordingly a matrix and also allows simple addressing of the individual recesses, for example in the manner as is conventional in checkerboards.

In one especially preferred configuration of the homogenization device in accordance with the invention, it is provided that at least one of the recesses is made as a blind hole with a bottom and surrounding wall. The recesses which are made as a blind hole are advantageous because production can take place efficiently, especially for round cross-sectional contours, by drilling, and the compensation element which has been inserted into one of the recesses made as a blind hole can be moved by interlocking only in one direction. Preferably, at least one subset of the recesses which are made as blind holes has the same geometry, as a result of which the efficiency of producing the recesses and the compensation elements is further increased.

Advantageously, at least one of the recesses made as a blind hole is located in the outer side of the carrier wall. The outer side as the side of the carrier wall facing away from the carrier interior is more easily accessible than an inner side facing the carrier interior, for which reason the recesses which are located in the outer side are more easily accessible.

Moreover, it is advantageous if an ejection opening which joining to the bottom of the blind hole of the recess is provided on the inner side of the carrier wall of at least one of the recesses formed as blind holes for ejecting the compensation element which has been inserted in the recess. One of the compensation elements which has been inserted into one of the recesses is ejected by applying a force to the compensation element through the ejection opening, the force being greater than the adhesive force of the compensation element in the ejection recess.

In one preferred configuration of the homogenization device in accordance with the invention, it is provided that at least one of the recesses has a recess axis, at least one of the compensation elements can be inserted into the recess solely by movement along the recess axis and the sole remaining translational freedom of the compensation element which has been inserted in the recess is along the recess axis. The insertion of the compensation element is accordingly a translational pushing or pressing into the recess. Preferably, in addition, there is at least one cover and the cover prevents the sole remaining translational freedom of at least one of the compensation elements which has been inserted into one of the recesses.

In one preferred configuration of the homogenization device in accordance with the invention, it is provided that in at least one of the recesses an internal thread is made and in at least one of the compensation elements an external thread is made so that the compensation element can be screwed into the recess. Screwing the compensation element into the recess allows much smaller adhesive friction between the compensation element and the recess for fixing the compensation element in the recess.

The compensation elements are formed at least partially of magnetic material. The magnetic material of at least one of the compensation elements can contain both soft magnetic material and also hard magnetic material. Accordingly, the totality of the compensation elements of a homogenization device can contain compensation elements whose magnetic material is either completely soft magnetic material or completely hard magnetic material. The magnetic material of any of the compensation elements can also contain any mixing ratio of soft magnetic material and hard magnetic material. Hard magnetic material differs from soft magnetic material by the higher remanence and higher coercive field strength. Consequently, the area of the hysteresis loop given between the magnetic flux density and the magnetic field strength for hard magnetic materials is greater than for soft-magnetic materials. Hard magnetic materials are better suited than soft magnetic materials for permanent magnets. Soft magnetic material is suited especially for routing a magnetic field due to the low magnetic resistance.

In one quite especially preferred configuration of the homogenization device in accordance with the invention, it is provided that the geometry of at least one of the compensation elements has a compensation element axis, the compensation element has preferably a longitudinal axis and the longitudinal axis coincides with the axis of the compensation element. The longitudinal axis is that axis of a body along which the body has its greatest spatial extension. Accordingly, the action of the compensation elements which have a longitudinal axis on the magnetic field is dependent on the orientation of the longitudinal axis relative to the magnetic field.

Compensation elements whose geometry has an axis can also be configured such that, along the axis of the compensation element, there is at least one layer of a magnetic material and at least one layer of a non-magnetic material. The non-magnetic layer makes it possible to adjust the distance of the magnetic material from the carrier interior and consequently also the action of the magnetic material on the magnetic field in the carrier interior.

In another preferred configuration of the homogenization device in accordance with the invention, it is provided that the axis of at least one of the compensation elements which has an axis and which has been inserted into one of the recesses is aligned by the recess at a given angle to the ideal magnetic field vector. Preferably, the alignment of the compensation element is parallel to the ideal magnetic field vector. The alignment of the axis of the compensation element at a given angle relative to the magnetic field enables not only the strength of the magnetic field in the carrier interior to be influenced, but also the magnetic field in the carrier interior to be shaped. But, generally a parallel alignment of the axes of the compensation elements to the ideal magnetic field vector is sufficient for homogenization of the magnetic field.

In another preferred configuration of the homogenization device in accordance with the invention, in which at least one of the compensation elements has an axis, the magnetic material has a preferred magnetic axis and the preferred axis coincides with the axis of the compensation element. A preferred magnetic axis is wherein the properties of the magnetic material of the compensation element along this axis differ from those along another axis perpendicularly to the preferred axis. Thus, for example, it can be provided that the remanence and/or the coercive force parallel to the preferred magnetic axis are greater than to an axis perpendicularly to the preferred axis.

With homogenization devices in accordance with the invention in which the magnetic material of at least one of the compensation elements contains hard magnetic material and the geometry has a compensation element axis, two alternative advantageous configurations are possible. In the first alternative configuration, the hard magnetic material is a permanent magnet and the magnet axis coincides with the axis of the compensation element. In the second alternative configuration, the compensation element which has been inserted into one of the recesses is, first of all, not macroscopically magnetized, but magnetization is provided after inserting of the permanent magnet into one of the recesses by a local magnetization magnetic field.

In particular, there are various possibilities for embodying and developing the homogenization device in accordance with the invention. For this purpose reference is made to the description of preferred exemplary embodiments in conjunction with the drawings.

BRIEF DESCRIPTION OF THE DRAWINGS

FIG. 1 shows an exemplary embodiment of a homogenization device in accordance with the invention, FIG. 2 shows an enlarged extract of the homogenization device which is shown in FIG. 1 and FIG. 3 shows a compensation element of a homogenization device in accordance with the invention.

DETAILED DESCRIPTION OF THE INVENTION

FIG. 1 shows the important components of an exemplary embodiment of a homogenization device 1 in accordance with the invention for homogenization of a magnetic field which has a non-magnetic carrier 2 and several compensation elements 3 formed of magnetic material. The non-magnetic material of the carrier 2 is aluminum and the magnetic material of which the compensation elements 3 is entirely neodymium-iron-boron. The carrier 2 has a carrier wall 4 and the carrier wall 4 surrounds the carrier interior 5. The carrier 2 has a one piece tubular form, and both the inner and outer cross-sectional contours of the carrier wall 4 are circles with a common center point. Also, other cross-sectional contours of the tubular carrier 2 are possible, thus, for example, a tubular carrier 2 with a staggered outer cross-sectional contour or a tubular carrier with rectangular inner and outer cross-sectional contour.

If the homogenization device 1 is located in a magnetic field, the magnetic field penetrates into the carrier interior 5 through a first carrier region 6 of the carrier wall 4 and emerges from the carrier interior 5 through a second carrier region 7 of the carrier wall 4. This exemplary embodiment of a homogenization device 1 in accordance with the invention is especially well suited to placement in a magnetic field of the magnetic field generating apparatus of one of the above mentioned nuclear magnetic flowmeters due to the shape of the carrier 2, since the measuring tube through which the medium is flowing and whose flow rate is to be determined can be routed through the carrier interior 5 and the carrier 2 can be easily attached to the nuclear magnetic flowmeter.

Both in the first carrier region 6 and also in the second carrier region 7 of the wall 4 of the carrier 2 are there a plurality of recesses 8, and the recesses 8 are located in the carrier wall 4, both in the first carrier region 6 and also in the second carrier region 7, each in a checkerboard pattern.

FIG. 2 shows an enlarged extract of the carrier wall 4 with several of the recesses 8 in a sectional view. The recesses 8 of the exemplary embodiment of a homogenization device 1 in accordance with the invention are, like the recesses 8 shown in FIG. 2, made as blind holes with each of the recesses 8 having a blind hole bottom 9 and a circumferentially surrounding blind hole wall 10. The carrier wall 4 has a outer side 11 and an inner side 12 which faces the carrier interior 5 and which is opposite the outer side 11, the recesses 8 being located in the outer side 11. There are also ejection recesses 13 in the carrier wall 4, each of the ejection recesses 13 lying in the inner side 12 of the carrier wall 4 and opening into the bottom 9 of the blind hole of a respective one of the recesses 8.

The geometry of the recesses 8 is the same. The shape has a longitudinal axis and a circular cross-sectional contour. Each of the recesses 8 also has an axis 14 which is aligned parallel to the ideal magnetic field vector and which coincides with the longitudinal axis. The geometry of the ejection recesses 13 is the same, having a longitudinal axis and a circular cross-sectional contour. However, the cross-sectional area of the ejection recesses 13 is smaller than the cross-sectional area of the recesses 8, as a result of which the bottoms of the blind holes have the shape of a circular ring and the circular ring constitutes the seat for the compensation element 3 which has been inserted into the respective recess 8. Both the recesses 8 and also the ejection recesses 13 are produced by drilling.

FIG. 1 shows that the exemplary embodiment of a homogenization device 1 in accordance with the invention also includes a cover 15. The cover 15 is a pipe whose inside diameter is matched to the outside diameter of the carrier 2 and can be pushed over the carrier 2. The cover 15 which has been pushed over the carrier 2 covers the recesses 8 which lie in the outer side 11.

FIG. 3 shows one of the compensation elements 3. The compensation elements 3 are a solid cylinder of magnetic material which has a longitudinal axis with the same geometry, and circular cross-sectional contour. Each of the compensation elements 3 also has an axis 16 which coincides with the longitudinal axis.

Each of the compensation elements 3 can be inserted directly into each of the recesses 8 by moving the respective compensation element 3 along the axis 14 of the respective recess 8 when the axis 14 of the recess and the axis 15 of the compensation element coincide. The sole remaining translational freedom of the compensation element 3 which has been inserted into the recess 8 is along the axis 14 of the recess. The inside diameter of the recess 8 and the outside diameter of the compensation element 3 are matched to one another such that there is adhesive friction between the wall 10 of the blind hole and the compensation element 3, where the adhesive friction is greater than the force generated by the other compensation elements 3 on the compensation element 3. The compensation elements 3 which have been inserted into the recesses 8 are accordingly fixed during the process of homogenization.

Each of the compensation elements 3 which has been inserted into a respective one of the recesses 8 can be removed by applying a force to the compensation element 3 through the ejection recess 13 that is greater than the adhesive force. The length of the compensation element 3 and the depth of the recesses 8 are matched to one another such that each of the compensation elements 3 which has been inserted into a respective one of the recesses 8 is both in contact with the bottom 9 of the blind hole of the recesses 8 and terminates at least partially flush with the outer side 11 of the carrier wall 4. If the cover 15 is pushed over the carrier 2, the cover 15 prevents movement of the compensation element 3 along the respectively sole remaining translational freedom, even if the forces which are acting on the compensation elements 3 exceed the adhesive forces.

What is claimed is:
1. A homogenization device for homogenization of a magnetic field, comprising: a non-magnetic cylindrical carrier having a carrier wall surrounding a carrier interior, wherein, with the homogenization device located in a magnetic field, the magnetic field penetrating into the carrier interior through a first carrier region of the carrier wall and emerging from the carrier interior through a second carrier region of the carrier wall and
   compensation elements formed at least partially of a magnetic material, each of the compensation elements being located at the carrier for contributing to homogenization of the magnetic field at least in the carrier interior,
   wherein a plurality of recesses are provided in the carrier wall matched in shape to the shape of the compensation elements and at least a respective one of the compensation elements being removably inserted directly in each of the recesses, wherein the shape of at least one of the compensation elements has a longitudinal compensation element axis which coincides with a longitudinal axis of at least one of the recesses, the longitudinal axes of the compensation elements and of the recesses both extend perpendicular to a longitudinal axis of the cylindrical carrier.

2. The homogenization device in accordance with claim 1, wherein at least one of the recesses is provided in at least one of the first carrier region and the second carrier region.

3. The homogenization device in accordance with claim 1, wherein at least one subset of the recesses forms a regular pattern in the carrier wall.

4. The homogenization device in accordance with claim 3, wherein the at least one subset of the recesses is in the form of a blind hole with a bottom and a circumferentially surrounding wall and the at least one subset of the recesses formed as blind holes having the same geometry.

5. The homogenization device in accordance with claim 4, wherein the carrier wall has an outer side and wherein at least one of the recesses in the form of a blind hole is in the outer side of the carrier wall.

6. The homogenization device in accordance with claim 5, wherein the carrier wall has an inner side and wherein an ejection is provided in the inner side of the carrier wall, the ejection opening joining to the bottom of the blind hole of the recess for enabling ejecting of the compensation element inserted in the recess.

7. The homogenization device in accordance with claim 1, wherein at least one of the recesses has a recess axis, at least one of the compensation elements being insertable solely by movement along the recess axis and the sole remaining translational freedom of the inserted compensation element being along the recess axis.

8. The homogenization device in accordance with claim 7, further comprising at least one cover which is mountable over the carrier in a manner that prevents movement of the inserted compensation element along the recess axis.

9. The homogenization device in accordance with claim 1, wherein in at least one of the recesses has an internal thread and at least one of the compensation elements has a matching external thread for enabling the at least one of the compensation elements to be screwed into the at least one of the recesses.

10. The homogenization device in accordance with claim 1, wherein the magnetic material of at least one of the compensation elements comprises at least one of a soft magnetic material and a hard magnetic material.

11. The homogenization device in accordance with claim 10, wherein the magnetic material is a hard magnetic material and wherein hard magnetic material is a permanent magnet having a magnet axis that coincides with an axis of the compensation element axis.

12. The homogenization device in accordance with claim 10, wherein the magnetization of the hard magnetic material of at least one of the compensation elements has been provided by a local magnetization magnetic field.

13. The homogenization device in accordance with claim 1, wherein that at least one of the compensation elements which has a compensation element axis has at least one layer of a magnetic material and at least one layer of a non-magnetic material.

14. The homogenization device in accordance with claim 11, wherein the compensation element axis of at least one of the compensation elements has a preferred magnetic axis that coincides with the magnetic axis of the magnetic material.

* * * * *